(12) United States Patent
Murayama et al.

(10) Patent No.: US 8,388,643 B2
(45) Date of Patent: Mar. 5, 2013

(54) BIOABSORBABLE POLYMERIC IMPLANTS AND A METHOD OF USING THE SAME TO CREATE OCCLUSIONS

(75) Inventors: Yuichi Murayama, Los Angeles, CA (US); Fernando Vinuela, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 2645 days.

(21) Appl. No.: 11/198,587

(22) Filed: Aug. 5, 2005

(65) Prior Publication Data

US 2006/0058835 A1    Mar. 16, 2006

Related U.S. Application Data

(63) Continuation-in-part of application No. 09/406,306, filed on Sep. 27, 1999, now Pat. No. 6,423,085.

(51) Int. Cl.
  *A61M 29/00* (2006.01)
  *B05D 7/00* (2006.01)
  *B28B 19/00* (2006.01)
  *C23C 18/00* (2006.01)
  *C23C 20/00* (2006.01)
  *C23C 28/00* (2006.01)
  *C23C 14/14* (2006.01)
  *C23C 14/16* (2006.01)
  *A61N 1/362* (2006.01)
  *A61B 1/00* (2006.01)

(52) U.S. Cl. .............. 606/200; 427/427.4; 427/527; 600/16; 600/104; 600/114

(58) Field of Classification Search ............... None
See application file for complete search history.

(56) References Cited

U.S. PATENT DOCUMENTS

| | | |
|---|---|---|
| 2,127,903 A | 8/1938 | Bowen |
| 3,562,820 A | 2/1971 | Braun |
| 4,902,508 A | 2/1990 | Badylak |
| 5,108,407 A | 4/1992 | Geremia |
| 5,122,136 A | 6/1992 | Guglielmi |
| 5,134,295 A | 7/1992 | Walischmiller |
| 5,141,747 A | 8/1992 | Scholz |
| 5,152,783 A | 10/1992 | Suzuki |
| 5,234,437 A | 8/1993 | Sepetka |
| 5,250,071 A | 10/1993 | Palermo |
| 5,261,916 A | 11/1993 | Engelson |
| 5,275,826 A | 1/1994 | Badylak |
| 5,304,194 A | 4/1994 | Chee |
| 5,308,704 A | 5/1994 | Suzuki |
| 5,350,397 A | 9/1994 | Palermo |
| 5,372,821 A | 12/1994 | Badylak |
| 5,386,012 A | 1/1995 | Strid |
| 5,423,849 A | 6/1995 | Engelson |
| 5,460,962 A | 10/1995 | Kemp |
| 5,522,836 A | 6/1996 | Palermo |
| 5,527,337 A | 6/1996 | Stack |
| 5,554,389 A | 9/1996 | Badylak |
| 5,582,619 A | 12/1996 | Ken |
| 5,599,326 A | 2/1997 | Carter |
| 5,624,449 A | 4/1997 | Pham |
| 5,624,461 A | 4/1997 | Mariant |
| 5,628,785 A | 5/1997 | Schwartz |
| 5,645,558 A | 7/1997 | Horton |
| 5,690,671 A | 11/1997 | McGurk |
| 5,700,258 A | 12/1997 | Mirigian |
| 5,733,329 A | 3/1998 | Wallace |
| 5,733,337 A | 3/1998 | Carr, Jr. |
| 5,743,905 A | 4/1998 | Eder |
| 5,749,891 A | 5/1998 | Ken |
| 5,823,198 A | 10/1998 | Jones |
| 5,830,879 A | 11/1998 | Isner |
| 5,891,192 A | 4/1999 | Murayama |
| 5,935,145 A * | 8/1999 | Villar et al. ............ 606/191 |
| 6,007,573 A | 12/1999 | Wallace |
| 6,015,424 A * | 1/2000 | Rosenbluth et al. ....... 606/200 |
| 6,423,085 B1 | 7/2002 | Murayama |
| 7,070,607 B2 | 7/2006 | Murayama |
| 2006/0058835 A1 | 3/2006 | Murayama |
| 2007/0093889 A1 | 4/2007 | Wu |

FOREIGN PATENT DOCUMENTS

| | | |
|---|---|---|
| JP | 11047138 | 2/1999 |
| JP | 11076249 | 3/1999 |
| WO | WO-9315787 | 8/1993 |
| WO | WO-9409705 | 5/1994 |
| WO | WO-9410936 | 5/1994 |
| WO | WO 9415534 | 7/1994 |
| WO | WO-9426175 | 11/1994 |
| WO | WO-9509659 | 4/1995 |
| WO | WO 9520916 | 8/1995 |
| WO | WO-9522611 | 8/1995 |

(Continued)

OTHER PUBLICATIONS

Van Der Giessen, "Marked Inflammatory Sequelae to Implantation of Biodegradable and Nonbiodegradable Polymers in Procine Coronary Arteries". 1996, Circulation—V94, No. 7, p. 1690.

*Primary Examiner* — Chang-Yu Wang
(74) *Attorney, Agent, or Firm* — Daniel L. Dawes; Marcus C. Dawes

(57) ABSTRACT

A embolic, bioabsorbable polymeric material (BPM) is incorporated into a coil to improve long-term anatomic results in the endovascular treatment of intracranial aneurysms. The material includes at least one biocompatible and bioabsorbable polymer and growth factors, is carried by hybrid bioactive coils and is used to accelerate histopathologic transformation of unorganized clot into fibrous connective tissue in aneurysms. An endovascular cellular manipulation and inflammatory response are elicited from implantation in a vascula location. Thrombogenicity of the biocompatible and bioabsorbable polymer is controlled by the composition of or proportioning the ratio of constituents making up the polymer. The biocompatible and bioabsorbable polymer is at least one polymer selected from the group consisting of polyglycolic acid, polyglycolic acid/poly-L-lactic acid copolymers, polycaprolactive, polyhydroxybutyrate/hydroxyvalerate copolymers, poly-L-lactide. Polydioxanone, polycarbonates, and polyanhydrides.

18 Claims, 11 Drawing Sheets

FOREIGN PATENT DOCUMENTS

| | | |
|---|---|---|
| WO | WO-9529647 | 11/1995 |
| WO | WO-9600035 | 1/1996 |
| WO | WO-9624661 | 8/1996 |
| WO | WO-9625179 | 8/1996 |
| WO | WO-9632146 | 10/1996 |
| WO | WO-9719643 | 6/1997 |
| WO | WO-9822158 | 5/1998 |
| WO | WO-9825545 | 6/1998 |
| WO | WO-9825636 | 6/1998 |
| WO | WO-9825637 | 6/1998 |
| WO | WO-9826291 | 6/1998 |
| WO | WO-9852623 | 11/1998 |
| WO | WO-9940852 | 8/1999 |
| WO | WO-9944538 | 9/1999 |
| WO | WO-0012016 | 3/2000 |
| WO | WO-0032112 | 6/2000 |
| WO | WO-0044306 | 8/2000 |
| WO | WO-02066091 | 8/2002 |

\* cited by examiner

BIOABSORBABLE POLYMERIC IMPLANTS AND A METHOD OF USING THE SAME TO CREATE OCCLUSIONS

RELATED APPLICATIONS

The present application is a continuation-in-part application of U.S. patent application Ser. No. 09/406,306 filed Sep. 27, 1999, now U.S. Pat. No. 6,423,085 which is incorporated herein by reference.

BACKGROUND OF THE INVENTION

1. Field of the Invention

The invention relates generally to the field of surgical and endovascular interventional instruments and specially to Intraluminal implants for occlusion of vessels or aneurysms.

2. Description of the Prior Art

Subarachnoid hemorrhage from intracranial aneurysm rupture remains a devastating disease. Endovascular occlusion of ruptured and unruptured intracranial aneurysms using Guglielmi detachable coil (GDC) technology has recently gained worldwide acceptance as a less-invasive treatment alternative to standard microsurgical clipping. However, critical evaluation of the long-term anatomical results of aneurysms treated with metal coils shows three limitations. First, compaction and aneurysm recanalization can occur. This technical limitation is more often seen in small aneurysms with wide necks and in large or giant aneurysms. Second, tight packing of metal coils in large or giant aneurysms may cause increased mass effect on adjacent brain parenchyma and cranial nerves. Third, the standard platinum metal coil is relative biological inert. Recent reports of methods to favorably enhance the biological activity of metal coils highlight the increased interest in finding innovative solutions to overcome these present biological limitations of the conventional metal coil system.

Recent animal investigations and post-mortem human histopathologic studies have provided valuable information on the histopathological changes occurring in intracranial aneurysms in patients treated with metal coils. Both animal and human studies support the hypothesis that a sequential biocellular process occurs in the aneurysm leading to the development of organized connective tissue after metal coil placement and altered hemodynamics. It has been postulated that the histological changes observed in an aneurysm after metal coil occlusion follow the general pattern of wound healing in a vessel wall. In support of metal coil-induced favorable histopathological transformation, in the largest post-mortem study reported, some aneurysms packed with metal coils demonstrated reactive fibrosis in the body of the aneurysm and anatomic exclusion of the orifice within six weeks after treatment.

What is needed is some means whereby this biological response can be transformed into an earlier and more intense wound healing or scarring.

What is needed is a method to promote an inflammatory response and healing of the aneurysm with reduction of its mass effect.

BRIEF SUMMARY OF THE INVENTION

The invention comprises a separable coil or implant which is comprised in turn of at least one biocompatible and bioabsorbable polymer or noncollagenous protein, and a placement device associated with the separable implant adapted to dispose the implant into a selected body lumen or cavity. While the illustrated embodiment describes an application in neurovascular surgery, it is expressly to be understood that the invention may be used to advantage in any body application where a stable occlusion is desired. Also while the illustrated embodiment describes a flexible coil having a bioactive layer disposed on its surface, the invention is usable with an implant taking any physical form or structure without limitation. For example, the coil may be fabricated entirely from the bioactive material or as a composite in combination with other nonbioactive materials. The implant may even be formed in situ as a self-adherent extruded implant having a cross-sectional shape determined by whatever extrusion die is provided at the end of the implantation catheter.

The biocompatible and bioabsorbable polymer or noncollagenous protein promotes an intra-aneurysmal inflammatory response and healing of the aneurysms. This device may carry growth factors, such as a vascular endothelial growth factor, a basic fibroblast growth factor or a mixture of several growth factors or cytokines.

The biocompatible and bioabsorbable polymer is in the illustrated embodiment at least one polymer selected from the group consisting of polyglycolic acid, poly~glycolic acid/poly-L-lactic acid copolymers, polycaprolactive, polyhydroxybutyrate/hydroxyvalerate copolymers, poly-L-lactide, polydioxanone. Polycarbonates, and polyanhydrides.

The biocompatible and bioabsorbable protein is at least one protein selected from the group consisting of fibrinogen, fibronectin, vitronectin, laminin, and gelatin.

In one embodiment the implant is composed of the biocompatible and bioabsorbable polymer or noncollagenous protein with a radio-opaque material is disposed thereon. Alternatively, the implant is composed of a radio-opaque material, and the biocompatible and bioabsorbable polymer or noncollagenous protein is disposed thereon.

The invention is also characterized as a method for forming a thrombus comprising the steps of providing a separable implant comprised at least in part of at least one biocompatible and bioabsorbable polymer or noncollagenous protein and disposing the separable implant into a body lumen or cavity including the various combinations and examples described above.

The method further of comprises the step of providing the implant with a growth factor, and in particular a vascular endothelial growth factor (VEGF), a basic fibroblast growth factor (bFGF), transforming growth factor (TGF), platelet derived growth factor (PDGF), or other growth factors.

The invention having been briefly summarized by the foregoing, the invention and its various embodiments may be better visualized by turning to the following drawings wherein like elements are referenced by like numerals.

Figure 1:
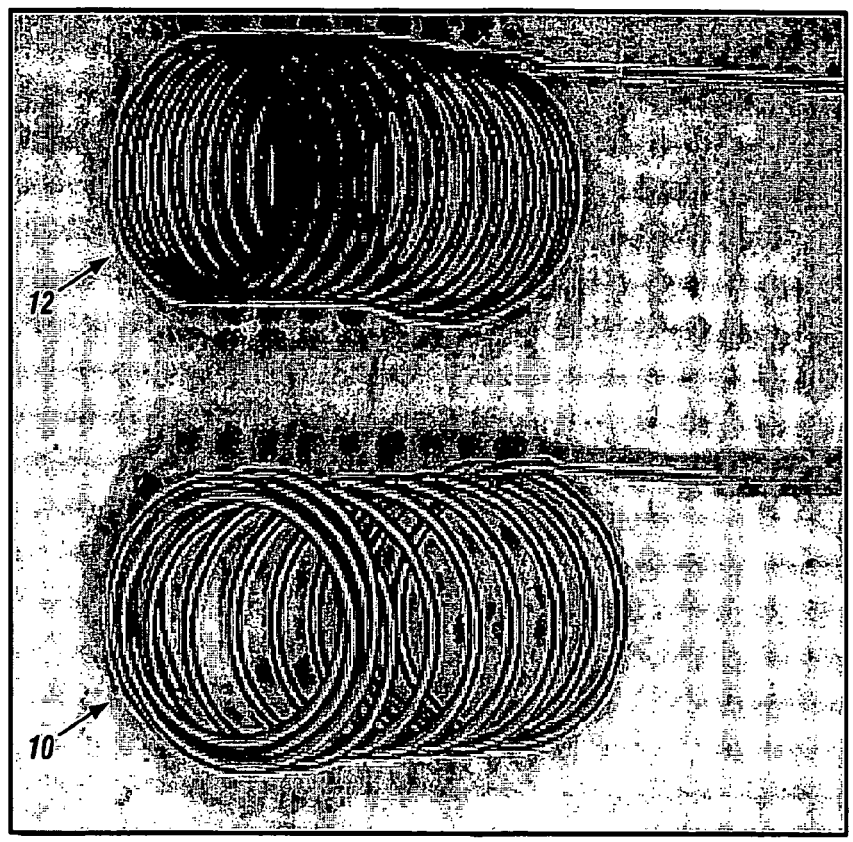
FIG. 1 is a photograph of two coils, a hybrid bioactive coil according to the invention shown at the top and conventional metal coil shown at the bottom. Both have similar mechanical structures and identical detachment systems.

The invention and its various embodiments may now be better understood by turning to the following illustrative description of the preferred embodiments.

DETAILED DESCRIPTION OF THE PREFERRED EMBODIMENTS

A new embolic agent, bioabsorbable polymeric material (BPM) is incorporated to a Guglielmi detachable coil (GDC) to improve long-term anatomic results in the endovascular treatment of intracranial aneurysms. The embolic agent, comprised at least in part of at least one biocompatible and bioabsorbable polymer and growth factors, is carried by hybrid bioactive coils and is used to accelerate histopathologic transformation of unorganized clot into fibrous connective tissue in experimental aneurysms. An endovascular cellular manipulation and inflammatory response are elicited from implantation in a vascular compartment or any intraluminal location. Thrombogenicity of the biocompatible and bioabsorbable polymer is controlled by the composition of the polymer, namely proportioning the amount polymer and copolymer in the coil or implant. The coil further is comprised at least in part of a growth factor or more particularly a vascular endothelial growth factor, a basic fibroblast growth factor or other growth factors. The biocompatible and bioabsorbable polymer is in the illustrated embodiment at least one polymer selected from the group consisting of polyglycolic acid, poly~glycolic acid/poly-L-lactic acid copolymers, polycaprolactive, polyhydroxybutyrate/hydroxyvalerate copolymers, poly-L-lactide. Polydioxanone, polycarbonates, and polyanhydrides.

Accelerating and modulating the aneurysm scarring process with bioactive materials overcomes the present long-term anatomic limitations of the metal coil system. Bioabsorbable polymers or proteins can be manufactured to have mechanical properties favorable for endovascular placement. Certain polymers and proteins can be constructed and altered to regulate adjacent tissue and cellular reaction. Moreover, selected polymers or proteins can also be used as delivery vehicles (e.g., continuous local delivery of growth factors). Bioabsorbable polymeric materials (BPM), such as polyglycolic acid and polyglycolic/poly-L-lactic acid copolymers, are well-studied and promising biocompatible substances that have been used in tissue engineering applications. Bioabsorbable polymeric materials promotes cellular reactions during its biological degradation. The degree of tissue reaction induced by bioabsorbable polymeric materials can be controlled by selecting polymer composition. Bioabsorbable polymeric materials can be utilized as a new bioabsorbable embolic material for the endovascular treatment of intracranial aneurysms. Compared to metal coils, bioabsorbable polymeric materials would offer the advantages of accelerated aneurysm scarring and negative mass effect. Before producing pure BPM coils, as part of a feasibility study, hybrid coils were developed, composed of a inner core of platinum wire and an outer braid of bioabsorbable polymeric materials. In general threads of bioabsorbable polymeric materials in any form may be attached in any manner to the platinum wire or coil. The core also need not be restricted to platinum, but any biocompatible and preferably bioabsorbable material for carrying the bioabsorbable polymeric materials can be substituted. For example, biocompatible plastics could be used either as coatings on metal or nonmetallic coils or out of which the entire coil could be composed.

The purpose of this study was to investigate whether hybrid bioactive coils accelerated the histopathological transformation of intra-aneurysmal unorganized clot to fibrosis and enhanced the formation of neointima across the aneurysm orifice, compared with standard metal coils in a swine aneurysm model.

In the present invention a bioabsorbable polymer (or protein) coils are used to control thrombosis or accelerate wound healing of the brain aneurysms for which platinum coils sometimes have often proven unsatisfactory.

Another aspect of the invention is a method of drug delivery system using bioabsorbable polymer (or proteins) in the combination with growth factors such as vascular endothelial growth factor (VEGF), basic fibroblast growth factor (bFGF) or other growth factors which promote long lasting effect of the wound healing These bioabsorbable coils are useful for treating giant brain aneurysms to prevent the mass effect on the brain parenchyma or cranial nerves by shrinkage of scaring aneurysm.

MODES FOR CARRYING OUT THE INVENTION

The implants of the invention may be placed within body lumens, e.g., blood vessels, Fallopian tubes, etc., of any mammalian species, including humans. The implant coils are made of biocompatible and bioabsorbable polymers or proteins. Examples of bioabsorbable polymers that have been used in the illustrated embodiment to make Intraluminal implants include but are not limited to polyglycolic acid, poly~gycolic/poly-L-lactic acid copolymers, polycaprolactive, polyhydroxybutyrate/hydroxyvalerate copolymers, poly-L-lactide, polydioxanone, polycarbonates, and polyanhydrides. Examples of bioabsorbable proteins that have been used in the illustrated embodiment to make Intraluminal implants include but are not limited to collagen, fibrinogen, fibronectin, vitronectin, laminin and gelatin.

To achieve radioopacity, the bioabsorbable polymer coils may be coated or mixed with radioopaque materials such as tantalum or platinum. The bioabsorbable polymer or protein itself may be mounted or coated onto coils or wires of metals such as platinum or nitonol.

Preferred growth factors for use in the invention are the naturally occurring mammalian angiogenic growth such as VEGF, or b-FGF. Mixtures of such growth factors may also be used if desired.

The bioabsorbable polymer coils of the invention can be placed within the body lumen, vascular system or vessels using procedures well known in the art. Generally, the desired site within the vessel is accessed with a catheter. For small diameter torturous vessels the catheter may be guided to the site by the use of guide wires. Once the site has been reached, the catheter lumen is cleared by removing guide wire. In the case of polymer occlusion coils, the coils are loaded by means of a pusher wire. The coils may be attached to the distal end of the pusher via a cleavable joint (e.g., a joint that is severable by heat, electrolysis, electrodynamic activation or other means) or a mechanical joint that permits the implant to be detached from the distal end of the pusher wire by mechanical manipulation. Alternatively, the coils may be free and detached from the pusher wire, simply pushed through the catheter and expelled from the distal end of the catheter.

Consider now the invention as illustrated by 24 experimental aneurysms which were created in twelve swine. For each animal, one aneurysm was embolized with bioactive coils of the invention as described below, and the other with metal coils. Hybrid bioactive coils were composed of an inner core platinum frame and outer core of bioabsorbable polymeric material as shown in FIGS. 1A, and 1B. FIG. 1 depicts a conventional metal coil 10 and a coil 12 which is a conventional metal coil on which has been disposed a layer of bioactive material. Any manner now known or later devised to dispose the bioactive material onto the coil is contemplated as being within the scope of the invention. For example, the bioactive layer may be coated, painted, sprayed, molded, cast, adhered, dipped, rolled, woven, sheathed or affixed to the metal coil.

In this embodiment polyglycolic/poly-L-lactic acid copolymers (PLGA) were used as the bioabsorbable polymeric material. Multi-filament braided polyglycolic/poly-L-lactic acid copolymers contained a 90/10 molar ratio of glycolic to L-lactic acid. The copolymer was heated and fixed on the core platinum frame. The percent volume of platinum was approximately 30% and of polymer 70% although the ratio is a matter of design choice. The inner platinum frame provided radio-opacity and coil shape memory. Platinum wire diameter of 0.00175 inch was used to match the stiffness of the standard metal coil system. Again this is a parameter of free design choice. A thin coat of a conventional biocompatible lubricant was placed over the bioabsorbable polymeric material to decrease friction during coil delivery. The hybrid bioactive coil was 0.32 mm in diameter (GDC-18 is 0.38 mm in diameter). In vitro evaluation showed that 90/10 PLGA began to lose tensile strength after five weeks and was completely absorbed within ten to twelve weeks.

Twelve Yorkshire swine were used in the study. The animals were 3 to 4 months old, weighed 30 to 40 kg, of mixed sex, and maintained on a standard laboratory diet. After an overnight fast, each swine was premedicated with intramuscular 20 mg/kg ketamine and 2 mg/kg xylazine. After endotracheal intubation, general anesthesia was maintained with mechanical ventilation and inhalation of 0.5% to 1.5% halothane.

Twenty-four lateral wall experimental aneurysms were constructed microcsurgically in bilateral common carotid arteries of 12 swine. Aneurysm sacs (8-12 mm) and necks (7 mm) were created of equal size, bilaterally. Aneurysm dimensions were recorded (height, width, length) at the time of creation and used in aneurysm volume and packing density estimation.

Figure 2A:
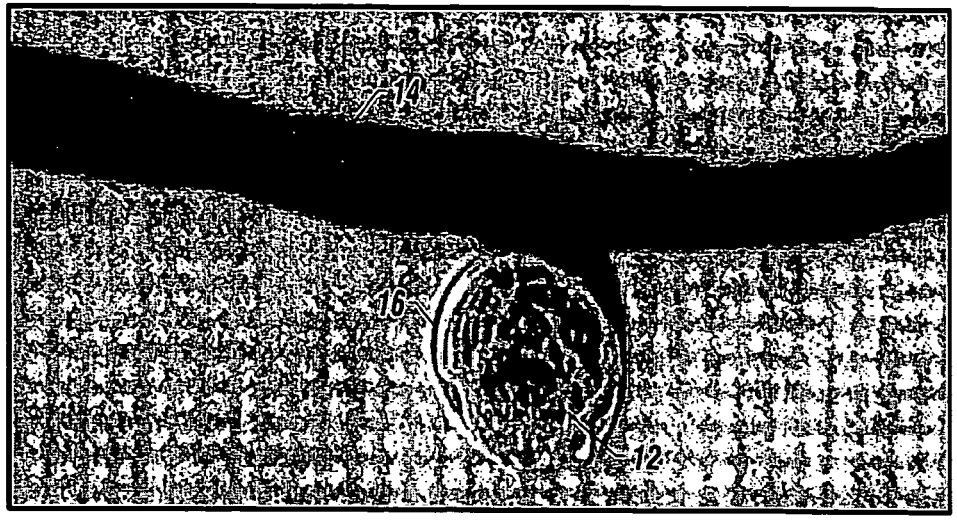
FIG. 2A is an immediate post-embolization digital subtraction angiogram (DSA) showing a lateral wall aneurysm loosely packed with hybrid bioactive coils. A neck remnant is present.

All endovascular procedures were performed immediately after aneurysm creation. A total of 24 experimental aneurysms were embolized with standard metal coil (n=12) or hybrid bioactive coils (n=12). For each swine, the type of coil, either hybrid bioactive or metal coil, to occlude the first aneurysm was randomly chosen. The contralateral aneurysm was then embolized with the other type of coil. A 6-F sheath was placed in the right femoral artery using standard Seldinger technique. Selective common carotid arteriograms were performed using a 6-F Fasguide guiding catheter (Boston Scientific/Target Therapeutics, Fremont, Calif.), showing the aneurysms in multiple projections. An intravenous bolus of 3000 U of heparin was injected to prevent thromboembolic complications. An Excel 14-microcatheter and Mizzen 10 microguidewire combination (Boston Scientific/Target Therapeutics, Fremont, Calif.) was advanced through the guiding catheter and the tip of the microcatheter was positioned in the center of the aneurysm. The aneurysms were densely packed with various sizes of coils. The goal of hybrid bioactive embolization was uniform coil placement in the aneurysm to achieve flow stagnation; therefore, tight packing was not always performed as shown in the angiogram of FIG. 2A, which depicts an aneurysm 16 connected to a vessel 14 in which a plurality of coils 12 have been disposed.

Figure 2B:
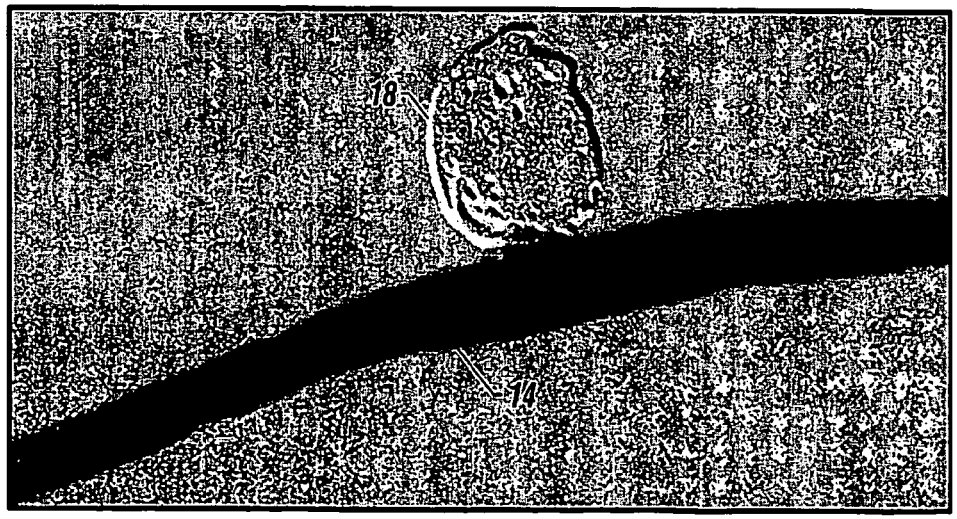
FIG. 2B is an immediate post-embolization DSA showing an aneurysm densely packed with metal coils. A small neck remnant is present.

All metal coil aneurysms 18 were tightly packed as shown in the angiogram of FIG. 2B. The mechanical characteristics of the hybrid bioactive coils 12 were evaluated during the endovascular procedures (trackability, pushability, smoothness, etc). A 14 day follow-up angiogram was performed in all cases, and 8 of 12 animals were then euthanized using standard approved procedures. The remaining 4 animals were kept alive for 3 months. Before the sacrifice of these 4 swine, three month follow-up angiograms were performed.

On follow-up angiograms, the distance between the coil mass and parent artery 14 at level of the center of aneurysm neck was measured as the angiographic manifestation of neointima formation. The presence of arterial stenosis/occlusion and intraluminal thrombus of the parent vessel at the level of the aneurysm neck was recorded. Aneurysm volumes were estimated using the formula, $V_a=(4/3)\pi(a/2)(b/2)(c/2)$ mm³ where $V_a$ is the aneurysm volume, a is the height, b is the width, and c is the length obtained at time of aneurysm creation. The volume of coils was estimated using the formula $V_c=\pi(OD/2)^2 \times L$ where $V_c$ is the coil volume, OD is the outside coil diameter, which for GDC-18 was 0.381 mm, GDC-10 was 0.254 mm, for bioactive hybrid coils was 0.32 mm, and where L is total collective length of the coils deployed in the aneurysm. The packing density (PD) for each aneurysm was calculated using the formula $PD=(V_c/V_a)\times 100\%$.

After the animals were euthanized using standard approved procedures, the parent arteries 14 of the aneurysm were cut and the necks of the aneurysms were analyzed macroscopically. The harvested aneurysms were fixed with 2% formaldehyde and sent to an outside institution for independent evaluation (P Al: Pathology Associate Inc., Frederick, Md.). The specimens were embedded in methylmethacrylate. Histological sections were cut using a diamond band saw. Longitudinal sections of the aneurysm were performed through the center of neck, approximately 50 .mu·m thick, polished and surface-stained with hematoxylin and eosin. The histopathological images were digitized using a high-resolution scanner (1000 dots per inch). Using low magnification views, the areas of unorganized thrombus in the aneurysm were calculated with the aid of the program, NIH Image 1.60. The histopathological thickness of neointima at the aneurysm neck was defined as the perpendicular distance from the line traced between anastomotic sutures closest to parent vessel 14 (7-0 proline) to the parent vessel lumen. This distance was calibrated by known coil diameter of GDC-18, 0.38 mm, and inner platinum diameter hybrid bioactive, 0.21 mm. Using high magnification views, the degree of cellular reaction around coils were graded 1 (minimal), 2 (mild), 3 (moderate), 4 (marked), and 5 (severe) by an independent pathologist.

Angiographic and histopathologic means of neointima thickness, means of percentage unorganized aneurysm thrombus, and means of packing density were statistically analyzed using an one-tailed paired student t-test. Mean grades of cellular reaction about coil groups were compared using the Wilcoxon signed rank test. For angiograms, proportions in each coil group with separation between coil mass and parent vessel were compared with Fisher's exact probabilities. Differences were considered significant for $P<0.05$.

The mechanical characteristics of the hybrid bioactive coils were slightly different than standard metal coils. The hybrid bioactive coils were slightly softer and smoother to push through the micro catheter during coil delivery into the aneurysm. It was possible to deliver and withdraw the hybrid bioactive coil from the aneurysm as many times as needed without increasing the friction of the coil or producing untoward coil stretching. The radio-opacity of the hybrid bioactive coil allowed good fluoroscopic visualization throughout the procedure.

Packing density of coils in each aneurysm group is listed in Table 1. Aneurysms embolized with bioactive hybrid coils were significantly less densely packed compared to metal coil treated aneurysms ($P<0.02$).

Figure 2C:
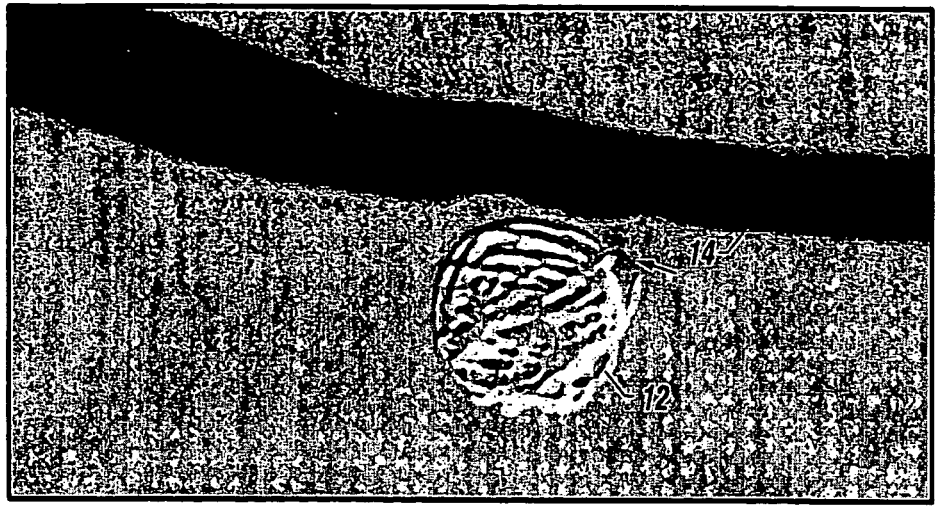
FIG. 2C is a fourteen-day follow-up DSA showing an aneurysm completely occluded by hybrid bioactive coils with remarkable separation between coil mass and parent artery, suggesting the formation of a neointima layer. No neck remnant is present.
Figure 2D:
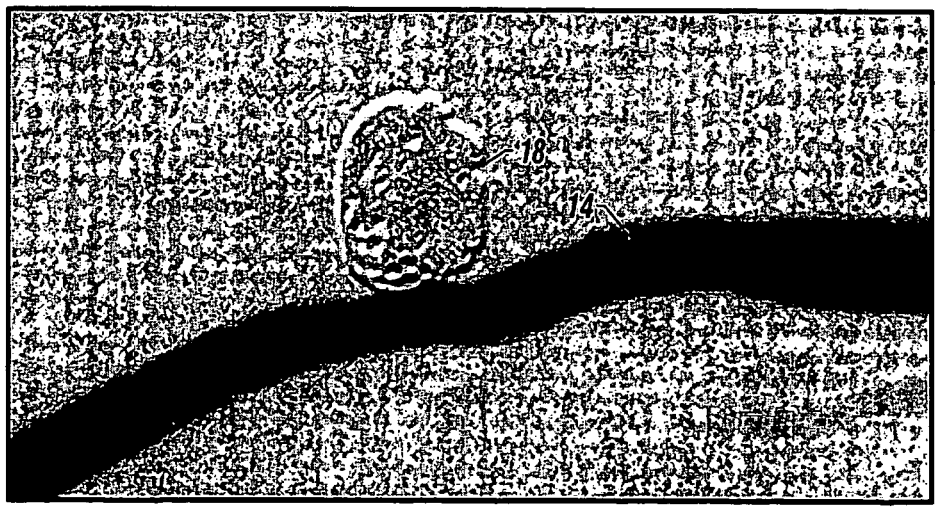
FIG. 2D is a fourteen-day follow-up DSA showing coil occlusion of an aneurysm treated with metal coils. There is no separation between coil mass and parent artery and a neck remnant persists.

Angiographical results 14 days after embolization are summarized in Table 2. Despite less dense packing, hybrid bioactive treated aneurysms showed complete occlusion as shown in FIG. 2C. Clear angiographic separation between the coil mass and parent artery 14 as seen in FIG. 2C, suggesting the development of thickened neointima, was present in 6 of 8 hybrid bioactive treated aneurysms, and in none of the metal coil aneurysms ($P<=0.01$). For the hybrid bioactive group, mean neointima thickness measured angiographically was 0.28±0.21 mm (mean±SD). For the metal coil group, no significant angiographical separation between coil mass and parent artery was seen. No hybrid bioactive aneurysm showed evidence of coil compaction or recanalization. Despite tight packing of the metal coil aneurysms, three out of 8 aneurysms embolized with metal coil showed small neck remnants as seen in FIG. 2D. In the hybrid bioactive group, no untoward thrombus formation or parent artery stenosis was evident.

Figure 2E:
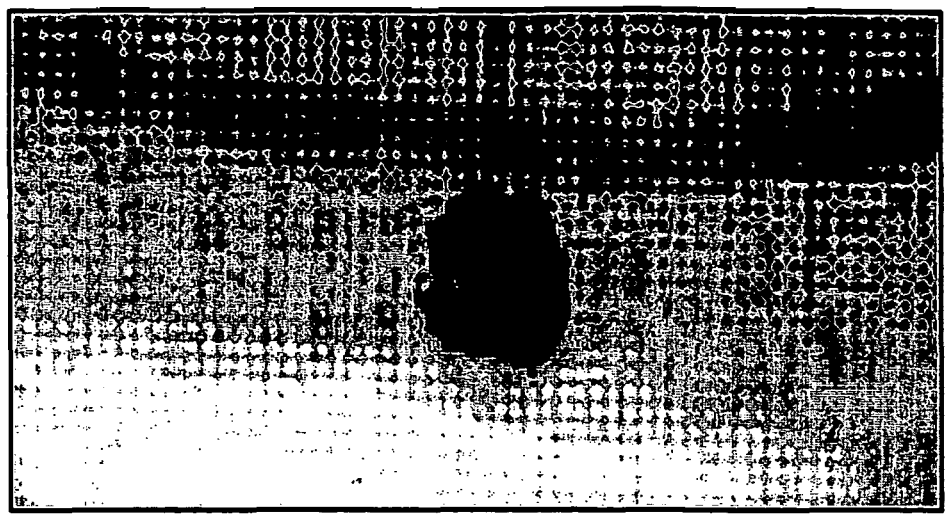
FIG. 2E is an immediate post-embolization angiogram showing lateral wall aneurysm tightly packed with metal coils. Small neck remnant is present.
Figure 2F:
FIG. 2F is an immediate-post-embolization with hybrid bioactive coils. The relatively loose packing is noted.
Figure 2G:
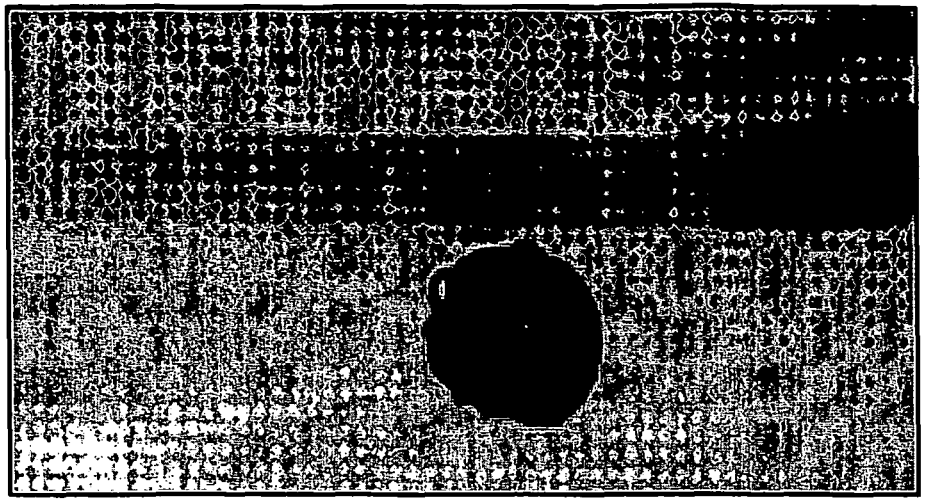
FIG. 2G is a three-month follow-up angiogram showing total occlusion of the aneurysm treated with metal coils. No definite angiographic separation between coil mass and parent artery is seen. The coil mass has not significantly changed shape.
Figure 2H:
FIG. 2H is a three-month follow-up angiogram showing complete occlusion of the aneurysm with hybrid bioactive coils. Definite separation between coil mass and parent artery has developed. Note the apparent flattening and contraction of the coil mass.

Table 3 summarizes the angiographical findings of 4 animals 3 months after treatment. Both metal coil and hybrid bioactive treated aneurysms were completely occluded. All hybrid bioactive aneurysms showed separation between coil mass and parent artery 14 (mean±SD; 0.45±0.12 mm) ($P=0.05$) while none of the metal coil aneurysms demonstrated this separation as depicted in FIGS. 2E and 2F. No evidence of untoward parent artery stenosis or thrombus formation was found. All aneurysms embolized with hybrid bioactive coils showed some degree of retraction compared with their original size. None of the metal coil aneurysms underwent major shape change or size reduction as depicted in FIGS. 2G and 2H.

Figure 3A:
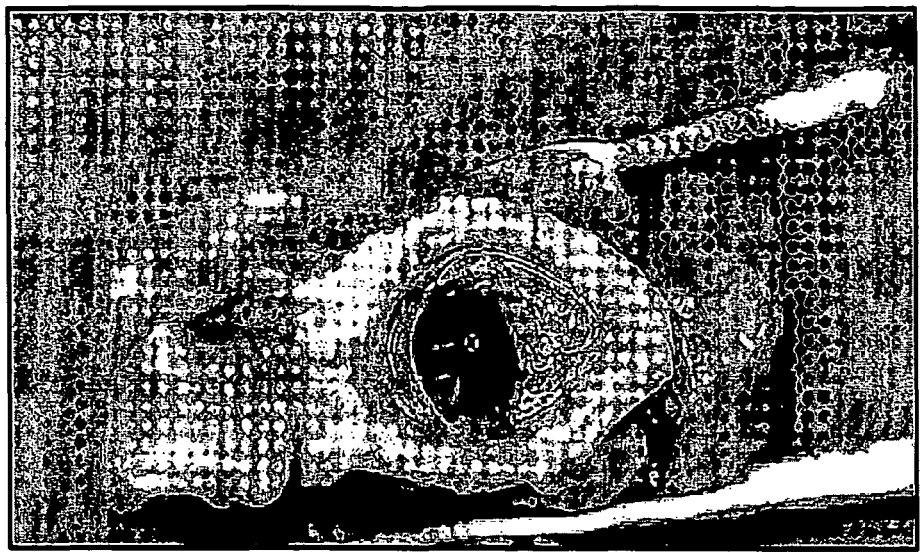
FIG. 3A is a macroscopic view of the aneurysm neck from the arterial lumen. The Aneurysm has been treated with conventional metal coils and shows partial covering of the neck with a thin white membrane. Portions of a metal coil remain visible. Note the gaps between the metal coils loops.
Figure 3B:
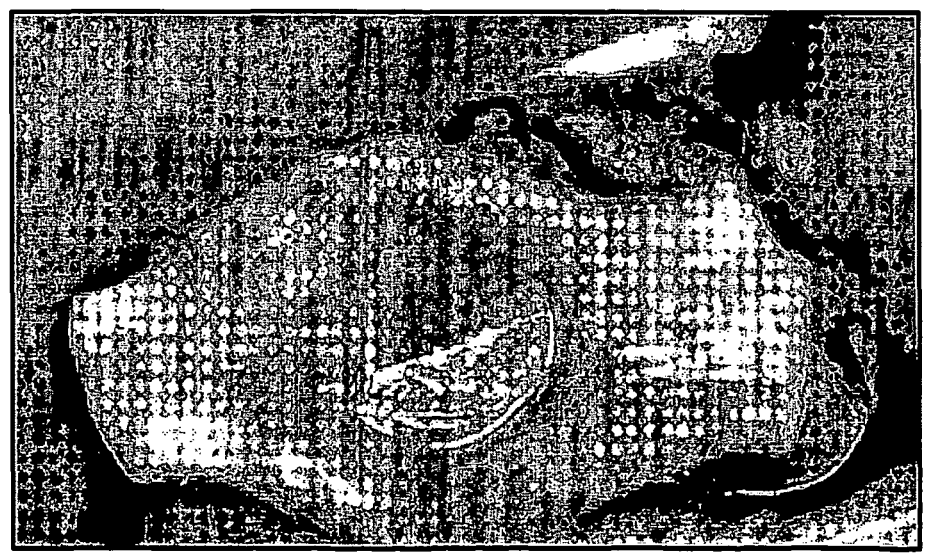
FIG. 3B is a macroscopic view of an aneurysm embolized by hybrid bioactive coils which aneurysm exhibits complete covering of the neck with a thick white tissue. There is no macroscopic gap at the aneurysm neck.

At 14 days, comparative macroscopic examination of aneurysm necks showed significant differences between the standard metal coil and the hybrid bioactive groups as shown in FIGS. 3A and 3B. Five of 8 aneurysms embolized with conventional metal coils had necks completely covered with a combination of reddish fibrous material and a thin membrane. The remaining three aneurysms embolized with metal coils showed partial neck coverage with a white membranous material. In the group formed from hybrid bioactive coils, a denser and thicker white fibrous tissue-response was observed at the aneurysm neck. The aneurysm orifices were covered with strong white fibrous tissue lined with neoendothelium arising from the edges of the neck of the aneurysm.

At 3 months, aneurysms embolized with conventional metal coils were solid and easy to dissect from surrounding tissue. The aneurysms embolized with hybrid bioactive coils were remarkably smaller and softer, suggesting contraction of the coil mass/aneurysm. Aneurysms occluded with metal coils and hybrid bioactive coils both demonstrated complete neck coverage with thick white connective tissue. Parent artery stenosis, thrombosis, or occlusion did not develop in either group.

Figure 4A:
FIG. 4A is a low magnification light microphotograph of a metal coil treated aneurysm 14 days after embolization. Intra-aneurysmal unorganized clot is present near the inflow zone and sac.
Figure 4B:
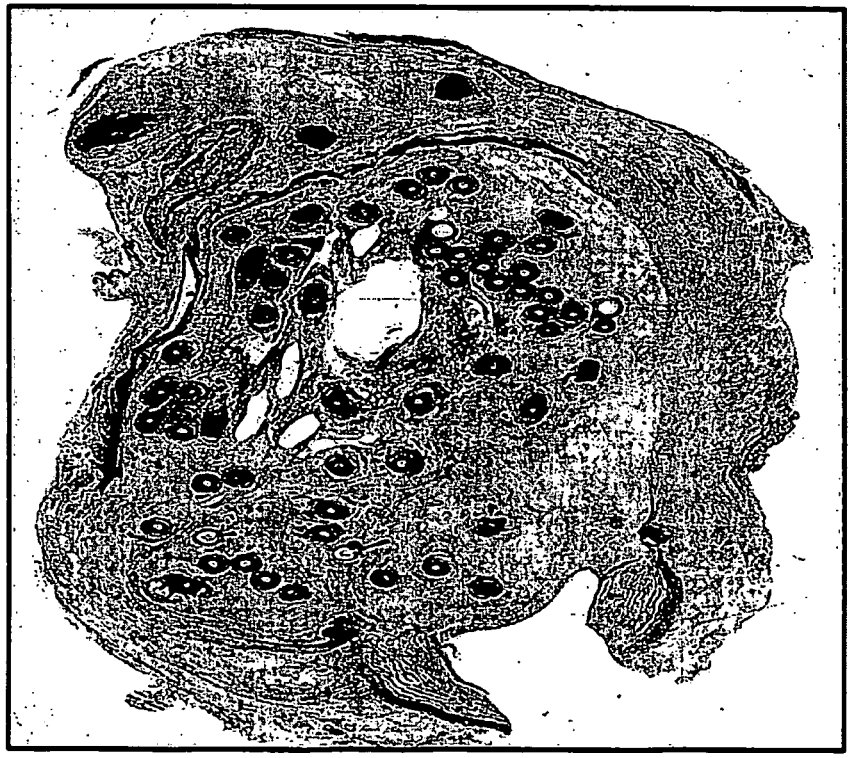
FIG. 4B is a low magnification light microphotograph of an aneurysm embolized with hybrid bioactive coils 14 days after embolization. There is clearly less unorganized clot near the inflow zone. Note the organized connective tissue across the aneurysm neck. Surgical sutures are visible and were used for intimal thickness measurement.
Figure 4C:
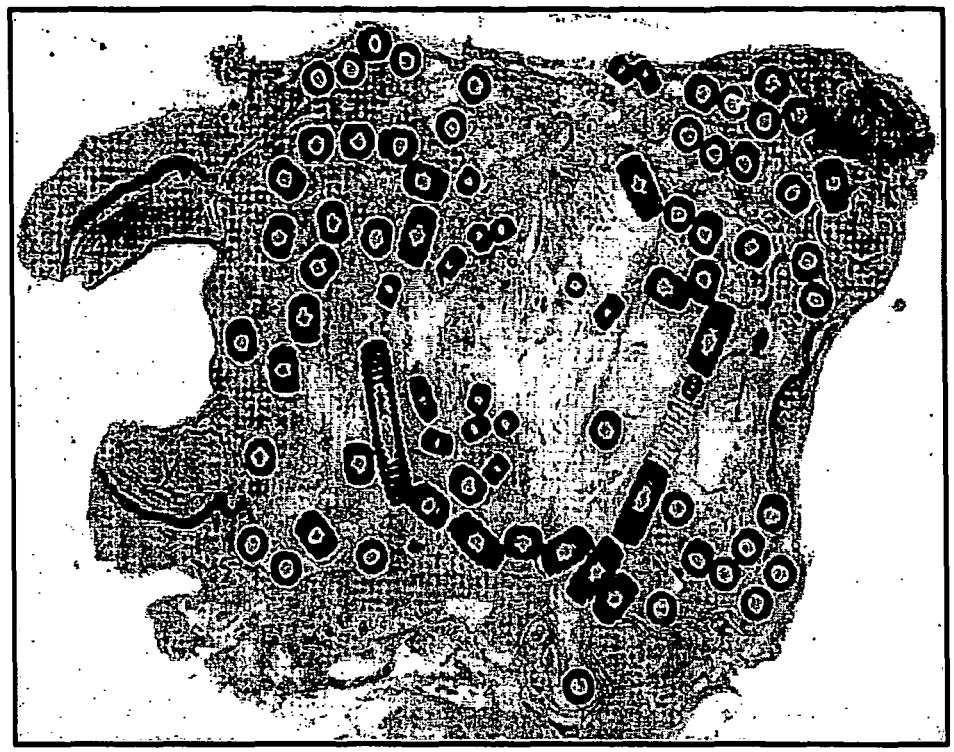
FIG. 4C is a low magnification light microphotograph of a metal coil treated aneurysm 3 months after embolization. The aneurysm sac is completely occluded with organized fibrous tissue, and there is thin neointima covering the neck.
Figure 4D:
FIG. 4D is a low magnification light microphotograph of an aneurysm treated with hybrid bioactive coils three months after embolization. The aneurysm sac is filled with mature fibrous tissue. Note the thickened neointima formation across the aneurysm neck.

Tables 4 and 5 summarize the histological low magnification findings 14 days and 3 months after embolization, respectively. At 14 days, aneurysms embolized with metal coils induced occlusions showed 37±15% (mean±SD) of intra-aneurysmal unorganized thrombus as seen in FIG. 4A. The hybrid bioactive aneurysms demonstrated 16±12% of unorganized thrombus (P<0.01) as depicted in FIG. 4B. At 3 months, metal coil induced occluded aneurysms were totally filled with an organized connective tissue and showed no evidence of unorganized thrombus as shown in FIG. 4C. Hybrid bioactive aneurysms showed similar histological findings as depicted in FIG. 4D.

Figure 5A:
FIG. 5A is a high magnification light microphotograph of a metal coil embolized aneurysm 14 days after treatment. Partial neointima formation at the neck is present indicated by the arrow. Unorganized thrombosis surrounds a coil segment.
Figure 5B:
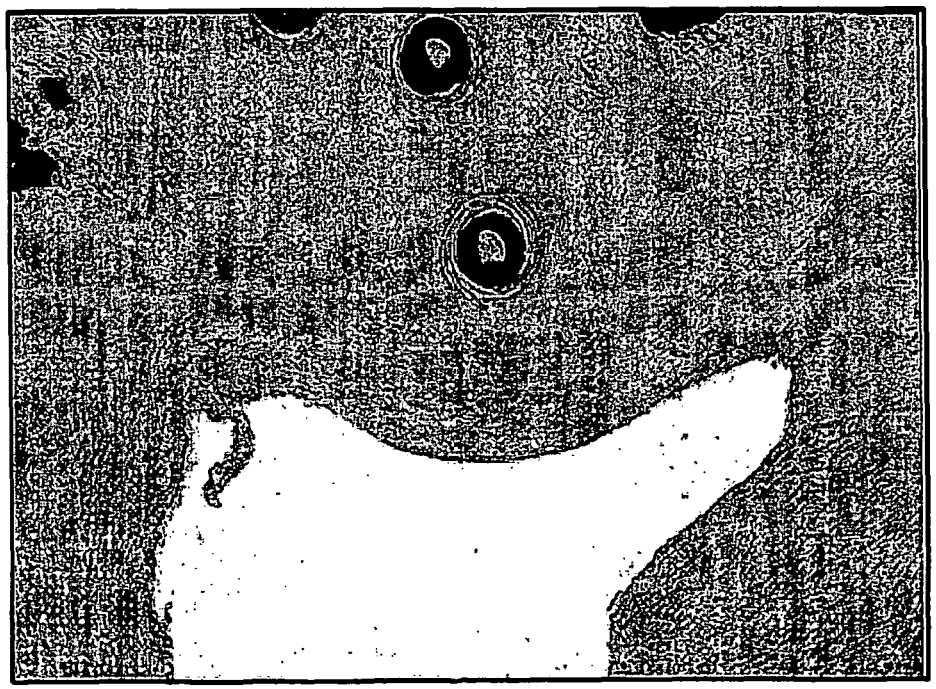
FIG. 5B is a high magnification light microphotograph of an aneurysm treated with hybrid bioactive coils 14 days after embolization. A thick layer of organized connective tissue covers the neck of the aneurysm.

At day 14, neointima thickness across the metal coil aneurysm necks measured at high magnification 0.24±0.21 mm (mean±SD) as depicted in FIG. 5A. Neck neointima thickness in hybrid bioactive induced aneurysms measured 0.65±0.26 mm (P<0.01) as depicted in FIG. 5B. At 3 months, neck neointima thickness measured 0.16±0.14 mm in metal coil occluded aneurysms and 0.73±0.37 mm (P<0.02) in hybrid bioactive occluded aneurysms.

Figure 5C:
FIG. 5C is a high magnification light microphotograph of a metal coil treated aneurysm 14 days after embolization. Soft connective tissue surrounds the coils and mild organized collagen and fibroblasts are present.
Figure 5D:
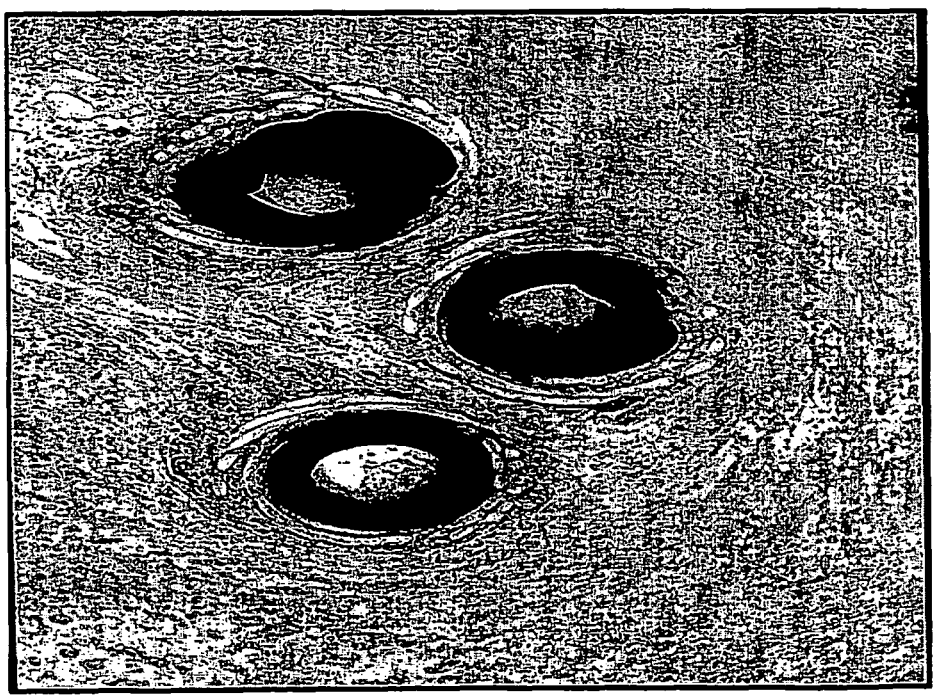
FIG. 5D is a high magnification light of an aneurysm 14 days after embolization using hybrid bioactive coils. The bioabsorbable polymeric outer braid is seen around the inner platinum core. Moderate inflammatory reaction is present, composed mainly of foreign body giant cells and macrophages. Some connective tissue with fibroblasts is appreciated between the coil loops and toward the periphery.

At day 14, high magnification light microscopy showed mildly organized connective tissue and fibroblasts surrounding standard metal coils near the necks of the aneurysms. The degree of cellular reaction around the coils was graded 1.6±0.7 as seen in FIG. 5C. Hybrid bioactive occluded aneurysms demonstrated moderate to marked connective tissue and mild to moderate inflammatory cell response around the coils, graded 3.0±0.9 (P<0.02). The dominant cells were fibroblasts and macrophages. A few foreign body giant cells were also found. Fibrous infiltration of the wall was also graded moderate to marked as shown in FIG. 5D.

Figure 5E:
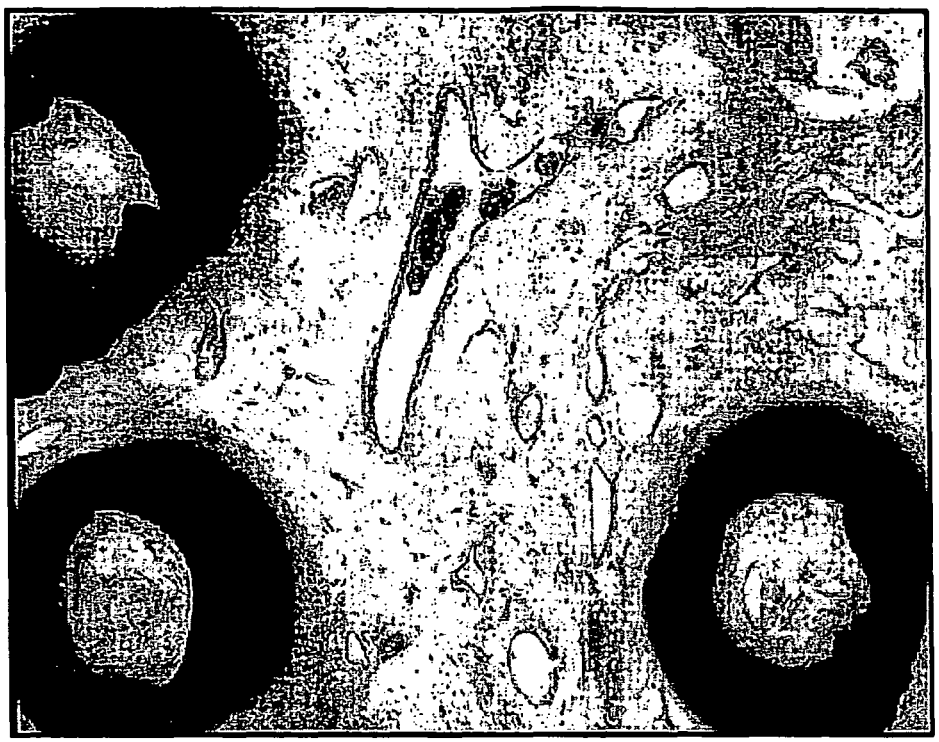
FIG. 5E is a high magnification light microphotograph of an aneurysm three months after metal coil embolization. Well-organized connective tissue surrounds the coils, with mild inflammatory reaction and development of moderate neo-angiogenesis. A neo-vascular channel covered with endothelial cells can be seen.
Figure 5F:
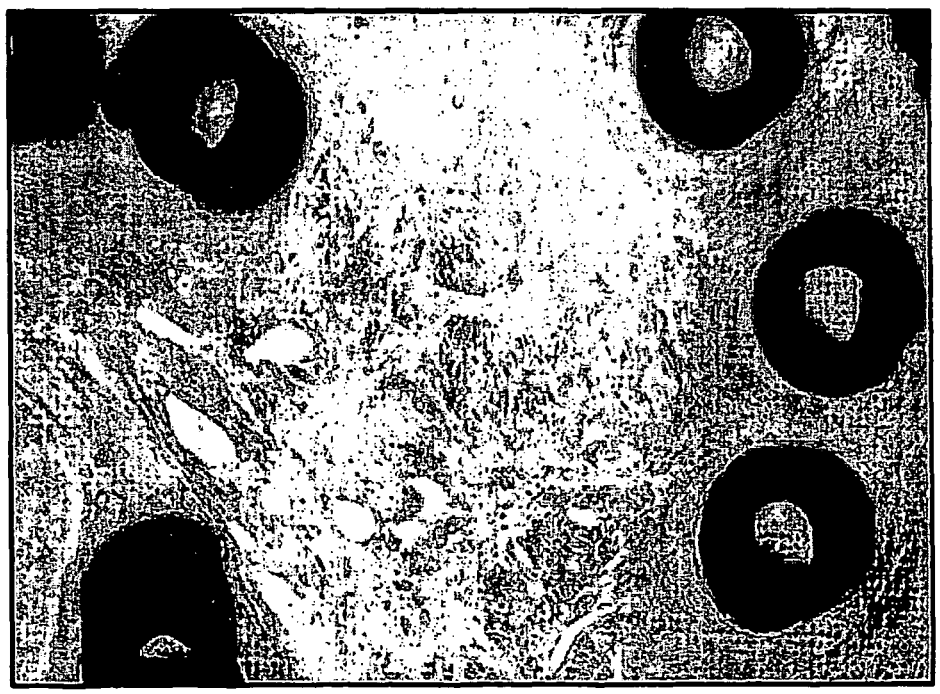
FIG. 5F is a high magnification light microphotograph of an aneurysm three months after being embolized by hybrid bioactive coils. The bioabsorbable polymeric material has been almost completely reabsorbed. Surrounding the coils is dense organized connective tissue with adjacent mild inflammatory response and angiogenic reaction.

At 3 months, metal coil occluded aneurysms showed minimal to moderate inflammatory reaction around the coils as seen in FIG. 5E. The sac was occupied with well-organized, mature mesenchymal fibrous tissue. There was also evidence of mild to moderate neo-angiogenesis with the development of small neo-vascular channels within the mesenchymal tissue. The necks of the aneurysms were covered with smooth fibrous neointima. In the occlusions induced by hybrid bioactive coils, mild to moderate infiltration of inflammatory cells still remained around the coils. The bioabsorbable polymer material was completely or near-completely absorbed as seen in FIG. 5F. The neo-angiogenesis in the connective tissue was mild. At 3 months, given small sample size, the differences in mean cellular reaction grade were not significantly different, 2.3±1.0 for occlusions induced by hybrid bioactive coils as compared to 1.3±0.5 for occlusions induced by metal coils (P=0.19).

The above experimental anatomical and histological results support the hypothesis that the hybrid bioactive coil does accelerate and intensify the degree of aneurysm scarring and neck neointima formation, compared to the standard metal coil. These favorable histological results were induced without untoward thrombosis, mechanical stenosis or occlusion of the parent common carotid artery 14. Comparative histological evaluation performed 14 days after endovascular procedure showed accelerated and more intense intra-aneurysmal transformation of unorganized clot to fibrous tissue and increased neck neointima formation in hybrid bioactive treated aneurysms. In particular, the extent of unorganized thrombus within the aneurysm sac was significantly less and the degree of cellular reaction around the coils was significantly more for the occlusions induced by the hybrid bioactive coils. At 3 months, the presence of organized connective tissue within the aneurysm and neointima formation across the neck remained more intense in the occlusions formed by the hybrid bioactive coils.

Despite relatively less dense packing in hybrid bioactive occluded aneurysms, a consistent retraction of the aneurysm and coil mass related to the development of scar tissue was observed at 3 months. At 3 months, all aneurysms, whether treated with metal coils or hybrid bioactive, were completely occluded and no significant histological differences were depicted except for increased neointima thickness in the hybrid bioactive group. These similar intra-aneurysmal long-term histological findings in both groups are not surprising and they may be explained in part by the natural tendency of experimental aneurysms in swine to spontaneous occlude. In the more chronic phases of inflammation and tissue repair in the swine aneurysm model, an equalization in cellular responses appeared to occur in metal coil and hybrid bioactive occluded aneurysms. Despite the limitations of porcine experimental lateral venous pouch aneurysms, these aneurysms after embolization have been shown to reconstitute a new arterial wall following a successful healing process, a process that we wish to stimulate and accelerate in human aneurysms treated by embolization. More importantly, the histological changes observed in our swine experimental aneurysm model appeared strikingly similar to those observed in limited human post-mortem aneurysms treated with metal coils in the acute to chronic phase (1 to 6 weeks).

It is hypothesized that the earlier and more intense organization of the aneurysm clot into scar tissue produced by hybrid bioactive coils can decrease coil compaction, aneurysm recanalization, and aneurysm recurrence. This accelerated histological response can lead to obvious clinical benefit in small aneurysms with wide necks and in large or giant aneurysms. The molecular and cellular reactions to the presence of metal coils in human intracranial aneurysms are starting to be understood. Despite the relative biological inertness of the standard platinum metal coil, a sequential process towards aneurysm scarring occurs. It has been postulated that aneurysm occlusion following metal coil embolization follows the biological pattern of wound healing in a vessel wall following a wide variety of traumatic or pathological conditions. Supporting this proposition are the results of the largest available human histopathological series of metal coil treated intracranial aneurysms (17 post-mortem and 1 surgically resected aneurysms collected from 16 patients). A probable evolution has been suggested within treated aneurysms from naked metal coils embedded in unorganized thrombus (up to 1 week) to incomplete replacement of intraluminal blood clot by fibrous tissue and partial membrane covering of the aneurysm orifice (1 to 6 weeks). Of the 16 aneurysms studied from 3 to 40 days after metal coil treatment, 6 aneurysms were completely occluded with formation of a thin membrane over the orifice, and an additional 5 aneurysms showed a thin incomplete membrane covering the neck of the aneurysm. Of note, the one giant, wide-necked aneurysm studied at 54 months after metal coil treatment showed only partial occlusion. However, the metal coils were densely incorporated in the aneurysm wall and embedded in a white fibrous mass. In one small aneurysm with a narrow neck, forty days after "100%" angiographic packing with metal coils, complete aneurysm sac fibrosis and complete aneurysm orifice coverage with neointima, including endothelial lining, was documented. Several animal studies have also supported the concept of aneurysm scarring after metal coil occlusion.

The use of bioabsorbable polymeric materials in biomedical engineering has dramatically increased during the past decade because of their interesting and well-studied properties. Bioabsorbable polymeric materials do not elicit intense chronic foreign body reaction because they are gradually absorbed and do not leave residua in the implantation site. In general, a faster degrading bioabsorbable polymeric material will result in a stronger inflammatory reaction. By altering polymer composition and therefore degradation times, intravascular inflammatory reactions may be controlled. Some bioabsorbable polymeric material has been found that is capable of regenerating tissue through the interaction of immunologic cells such as macrophages.

Bioabsorbable polymeric material as an embolic material for the treatment of the intracranial aneurysms may offer three main advantages that are capable of overcoming the current anatomical limitations of the metal coil system. First, bioabsorbable polymeric material stimulates mild to strong cellular infiltration and proliferation in the process of degradation that can accelerate fibrosis within aneurysms. Accelerated fibrosis within the aneurysm will likely lead to stronger anchoring of coils. The more connective tissue and less unorganized clot the more resistant the aneurysm will be to the "water hammer" effect of pulsatile blood. Therefore, accelerated scar formation can potentially prevent coil compaction and aneurysm recanalization. Second, organized connective tissue filling an aneurysm tends to retract over time due to maturation of collagen fibers (scar tissue). This connective tissue retraction can reduce aneurysm size and it may decrease aneurysm compression on brain parenchyma or cranial nerves. This concept is supported by our animal study. All 3 month follow-up aneurysms treated with hybrid bioactive coils showed size reduction. Although the duration of symptoms is the major determinant of clinical improvement for patients suffering from aneurysm mass effect, scar retraction of aneurysms should be better tolerated than permanent metallic implants. Third, coil thrombogenicity is an important property of an embolic device. In an in vitro study using radioactively labeled platelet (Indium) bioabsorbable polymeric material was found to be 50% less thrombogenic than metal coils. Bioabsorbable polymeric material may accelerate aneurysm healing with less thrombogenicity. Other advantages of bioabsorbable polymeric material include their shape versatility, cheaper cost of manufacture, and potential use as a drug delivery vehicle. Various proteins, cytokines, and growth factors can be potentially implanted in bioabsorbable polymeric material and slowly delivered during bio-absorption. The concept of a drug delivery system using bioabsorbable polymeric material has much potential for controlled healing of aneurysms in the future.

In this experimental animal study, we used 90/10 PLGA as the bioabsorbable polymeric material. It has a slow degradation and bio-absorption time and elicits a relatively mild inflammatory reaction. Therefore, the potential risk of untoward overly aggressive inflammatory response in the parent vessel, causing stenosis or occlusion, is minimized and unlikely. Glycolide/Lactide-based bioabsorbable polymer is widely used in medicine. It is used in sutures, cranioplasty material, drug delivery systems, and stents. Bioabsorbable polymeric material was found to be completely absorbed within 3 months in our animals.

The hybrid bioactive coil utilizes the well-established metal coil delivery and detachment system and benefits from the radio-opacity of the platinum core. The hybrid bioactive coil is slightly softer and has less friction than conventional metal coils during coil delivery, and it has less intrinsic memory.

Thus, in summary comparative angiographic and histopathologic data analyzed at two weeks and at three months after embolization showed the following as summarized in Tables 4 and 5. At 14 days, 6 of 8 aneurysms induced by bioactive coils had angiographic evidence of neck neointima as compared to the finding that none of the eight aneurysms induced by metal coil ($P<0.05$) did. At 3 months, four of the four aneurysms induced by bioactive coils were smaller and had angiographic evidence of neck neointima as compared to the finding that none of the four aneurysms induced by metal coils ($P=0.05$) did. At 14 days, histologic analysis of aneurysm healing favored aneurysms induced by bioactive coils (all $P<0.05$): grade cellular reaction about coils $3.0\pm0.9$ (mean$\pm$SD) for aneurysms induced by bioactive coils as compared to $1.6\pm0.7$ for aneurysms induced by metal coils; percentage unorganized thrombus $16\%\pm12\%$ for aneurysms induced by bioactive coils as compared to $37\%\pm15\%$ for aneurysms induced by metal coils; neck neointima thickness $0.65\pm0.26$ mm for aneurysms induced by bioactive coils as compared to $0.24\pm0.21$ mm for aneurysms induced by metal coils. At 3 months, only neck neointima thickness was significantly different ($P<0.05$), $0.73\pm0.37$ mm for aneurysms induced by bioactive coils as compared to $0.16\pm0.14$ mm for aneurysms induced by metal coils.

In experimental swine aneurysms, the bioactive coils of the invention accelerated aneurysm fibrosis and intensified neck neointima formation without causing parent artery stenosis or thrombosis. Bioactive coils may improve long-term anatomical outcome of standard metal coils by decreasing aneurysm recanalization due to stronger in-situ anchoring of coils by organized fibrous tissue. The retraction of this scar tissue may also decrease the size of aneurysms and clinical manifestations of mass effect observed in large or giant aneurysms.

In further summary, compared to standard metal coils, hybrid bioactive coils accelerated the transformation of intraaneurysmal unorganized clot into scar tissue. The histological findings were dramatically different 14 days after embolization and were less different at 3 months. Hybrid bioactive coils can be utilized in the clinical setting without significant technical differences from current metal coil techniques and their use may not require tight packing of the aneurysms to achieve a long-term complete anatomical cure.

Coils which are made only of a bioabsorbable polymeric material will improve long-term anatomical outcome of patients with ruptured and unruptured intracranial aneurysms by further decreasing coil remodeling and aneurysm recanalization. Coils made entirely of bioabsorbable polymeric materials will also have a positive clinical impact in patients presenting with mass effect related to aneurysm compression of brain parenchyma or cranial nerves.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

For example, it has been found that occlusion according to the invention can be satisfactorily achieved without the inclusion of any proteins in the occluding material on or in the coil or implanted object. Thus, while the invention contemplates the presence of noncollagenous proteins as part of the occluding object, it is expressly to be understood that the invention also contemplates the absence of any proteins as well.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

TABLE 1

Packing density[1,2] comparison.

| Swine | BPM/GDC | GDC |
|---|---|---|
| 1 | 13% | 22% |
| 2 | 18% | 39% |
| 3 | 12% | 14% |
| 4 | 26% | 26% |
| 5 | 17% | 15% |
| 6 | 16% | 22% |
| 7 | 15% | 16% |
| 8 | 20% | 14% |
| 9 | 19% | 25% |
| 10 | 18% | 55% |
| 11 | 27% | 44% |
| 12 | 22% | 46% |
| Mean ± SD | 19 ± 4% | 28 ± 14% |

[1]Aneurysm volumes were estimated using the formula $Va = (4/3)\pi(a/2)(b/2)(c/2)$ mm$^3$ (Va: aneurysm volume, a: height, b: width, C: length; dimensions obtained at time of aneurysm creation). The volume of coils was estimated using the formula $Vc = \pi(OD/2)^2 \times L$ (Vc: coil volume, OD: outside coil diameter, GDC-18 0.381 mm, GDC-10 0.254, BPM/BDC 0.32 mm, L: total length of coils deployed in the aneurysm). The packingdensity (PD) for each aneurysm was calculated using the formula $PD = (Vc/Va) \times 100$.
[2]$P < 0.02$ Mean packing density for BPM/GDC significantly less than for GDC.

TABLE 2

Angiographic findings immediate post-embolization and 14 days after embolization.[1,2]

| Coil | Initial occlusion | Final occlusion | Angiographical neck thickness(mm) |
|---|---|---|---|
| GDC1 | complete | complete | 0 |
| GDC2 | near complete | complete | 0 |
| GDC3 | near complete | neck remnant | 0 |
| GDC4 | complete | complete | 0 |
| GDC5 | neck remnant | neck remnant | 0 |
| GDC6 | near complete | complete | 0 |
| GDC7 | near complete | complete | 0 |
| GDC8 | near complete | neck remnant | 0 |
| BPM/GDC1 | contrast filling | complete | 0 |
| BPM/GDC2 | neck remnant | complete | 0.2 |
| BPM/GDC3 | complete | complete | 0.5 |
| BPM/GDC4 | near complete | complete | 0 |
| BPM/GDC5 | near complete | complete | 0.5 |
| BPM/GDC6 | contrast filling | complete | 0.5 |
| BPM/GDC7 | neck remnant | complete | 0.2 |
| BPM/GDC8 | contrast filling | complete | 0.3 |

[1]Angiographical findings
contrast filling: contrast filling in the sac of the aneurysm
neck remnant: contrast filling at the base of the aneurysm
near complete: some coil loops exsist in the neck remnant
complete: no contrast filling in entire aneurysm sac
[2]Measurement of thickness performed at the center of the aneurysm neck.

TABLE 3

Angiographic findings 3 months after embolization.

| Coil | Initial occlusion | Final occlusion | Angiographic neck thickness (mm) | Size reduction |
|---|---|---|---|---|
| GDC9 | complete | complete | 0 | no |
| GDC10 | near complete | complete | 0 | no |
| GDC11 | near complete | complete | 0 | no |
| GDC12 | complete | complete | 0 | no |
| BPM/GDC9 | near complete | complete | 0.5 | yes |
| BPM/GDC10 | complete | complete | 0.3 | yes |
| BPM/GDC11 | contrast filling | complete | 0.4 | yes |
| BPM/GDC12 | neck remnant | complete | 0.6 | yes |

TABLE 4

Histological results 14 days after embolization.

| Coil | Percentage of unorganized thrombus | Neointima thickness (mm) | Histological inflammation grade near coils |
|---|---|---|---|
| GDC1 | 46% | 0.30 | 2 |
| GDC2 | 54% | 0.22 | 1 |
| GDC3 | 31% | 0.53 | 1 |
| GDC4 | 20% | Herniation | 2 |
| GDC5 | 36% | 0.44 | 1 |
| GDC6 | 51% | Herniation | 3 |
| GDC7 | 13% | 0 | 2 |
| GDC8 | 47% | 0 | 1 |
| Mean ± SD | 37 ± 15% | 0.24±0.21 | 1.6 ± 0.7 |
| BPM/GDC1 | 32% | 0.54 | 2 |
| BPM/GDC2 | 30% | 0.97 | 3 |
| BPM/GDC3 | 21% | 0.93 | 2 |
| BPM/GDC4 | 0% | 0.7 | 3 |
| BPM/GDC5 | 16% | 0.62 | 2 |
| BPM/GDC6 | 20% | 0.13 | 4 |
| BPM/GDC7 | 2% | 0.64 | 4 |
| BPM/GDC8 | 7% | 0.65 | 4 |
| Mean ± SD | 15 ± 12% | 0.65 ± 0.26 | 3.0 ± 0.9 |
| P-Value | $P < 0.01$ | $P < 0.01$ | $P < 0.02$ |

TABLE 5

Histological results 3 months after embolization.

| Coil | Percentage of unorganized thrombus | Neointima thickness (mm) | Histological inflammation grade near coils |
|---|---|---|---|
| GDC9 | 0 | 0.13 | 1 |
| GDC10 | 0 | 0.36 | 1 |
| GDC11 | 0 | 0.13 | 2 |
| GDC12 | 3% | 0.0 | 1 |
| Mean ± SD | 0.75 ± 1.5% | 0.16 ± 0.14 | 1.3 ± 0.5 |

TABLE 5-continued

Histological results 3 months after embolization.

| Coil | Percentage of unorganized thrombus | Neointima thickness (mm) | Histological inflammation grade near coils |
|---|---|---|---|
| BPM/GDC9 | 3% | 0.55 | 2 |
| BPM/GDC10 | 0 | 1.28 | 3 |
| BPM/GDC11 | 0 | 0.43 | 1 |
| BPM/GDC12 | 0 | 0.67 | 3 |
| Mean ± SD | 0.75 ± 1.5% | 0.73 ± 0.37 | 2.3 ± 1.0 |
| P-Value | NS[1] | P < 0.02 | P = 0.19 |

[1]NS = not statistically significant, P > 0.05

We claim:

1. A method for occluding a vascular aneurysm comprising:
   disposing a separable implant into the aneurysm, which implant is permanently retained within the aneurysm at least until bioabsorption of the implant, if at all; and
   selectively inducing a selected degree of controlled formation of scar tissue in the aneurysm to occlude substantially the entire aneurysm without formation of scar tissue in excess of that needed for occlusion by means of a bioreaction to a substance forming at least part of the implant, the degree of formation of scar tissue being controlled according to selection of the constituents of the substance and their relative ratios.

2. The method of claim 1 where the degree of formation of scar tissue being controlled according to control of the substance comprises predetermining constituent composition ratios of the substance.

3. The method of claim 2 where inducing controlled formation of scar tissue in the aneurysm without formation of scar tissue in excess of that needed for occlusion by means of a bioreaction to a substance comprises permanently implanting a controlled mixture of noncollagenous proteins in the aneurysm at least until bioabsorption of the mixture, if at all.

4. The method of claim 3 further comprising permanently implanting a growth factor with the controlled mixture of noncollagenous proteins into the aneurysm at least until bioabsorption of the growth factor, if at all.

5. The method of claim 4 wherein permanently implanting the growth factor comprises permanently implanting a basic fibroblast growth factor.

6. The method of claim 1 wherein inducing controlled formation of scar tissue in the aneurysm without formation of scar tissue in excess of that needed for occlusion by means of a bioreaction to a substance comprises permanently implanting a mixture composed of a predetermined ratio of copolymers selected from the group consisting of polyglycolic acid, poly-glycolic acid/poly-L-lactic acid copolymers, polycaprolactive, polyhydroxybutyrate/hydroxyvalerate copolymers, poly-L-lactide, polydioxanone, polycarbonates, and polyanhydrides, the ratio being selected to control the degree of inflammatory response.

7. The method of claim 3 wherein permanently implanting a controlled mixture of noncollagenous proteins comprises permanently implanting a mixture including at least one protein selected from the group consisting of fibrinogen, fibronectin, vitronectin, and laminin.

8. The method of claim 1 where inducing controlled formation of scar tissue in the aneurysm is controlled to avoid intense chronic foreign body reaction.

9. The method of claim 1 where inducing controlled formation of scar tissue in the aneurysm is controlled to provide a controlled degradation time.

10. The method of claim 1 where inducing controlled formation of scar tissue in the aneurysm is controlled to regenerate tissue through the interaction of immunologic cells.

11. The method of claim 1 where inducing controlled formation of scar tissue in the aneurysm is controlled to stimulate cellular infiltration and proliferation in the process of degradation to accelerate fibrosis.

12. The method of claim 11 where stimulating cellular infiltration and proliferation in the process of degradation to accelerate fibrosis more strongly anchors the implant than the degree to which metal coils are anchored in aneurysms.

13. The method of claim 1 where inducing controlled formation of scar tissue in the aneurysm is controlled to generate more connective tissue and a less unorganized clot than metal coils so that the aneurysm in which the implant is disposed is more resistant to a water hammer effect of pulsatile blood than when treated by metal coils.

14. The method of claim 1 where inducing controlled formation of scar tissue in the aneurysm is controlled to restrict compaction of the implant.

15. The method of claim 1 where inducing controlled formation of scar tissue in the aneurysm is controlled to restrict aneurysm recanalization by accelerated scar formation.

16. The method of claim 1 where inducing controlled formation of scar tissue in the aneurysm is controlled to induce organized connective tissue to fill the aneurysm and to retract the aneurysm over time due to maturation of collagen fibers to reduce aneurysm size and to decrease aneurysm compression on brain parenchyma or cranial nerves.

17. The method of claim 1 where inducing controlled formation of scar tissue in the aneurysm is controlled to occlude the aneurysm and to accelerate aneurysm healing without increasing thrombogenicity more than that induced by metal coils.

18. The method of claim 1 further comprising gradually absorbing the substance without leaving residua in the aneurysm.

* * * * *

UNITED STATES PATENT AND TRADEMARK OFFICE
CERTIFICATE OF CORRECTION

PATENT NO. : 8,388,643 B2  
APPLICATION NO. : 11/198587  
DATED : March 5, 2013  
INVENTOR(S) : Yuichi Murayama and Fernando Vinuela Page 1 of 1

It is certified that error appears in the above-identified patent and that said Letters Patent is hereby corrected as shown below:

In the Specifications:

At col. 1, line 4, insert:

-- This invention was made with Government support under Grant No. NS042316 awarded by the National Institutes of Health. The Government has certain rights in this invention. --

Signed and Sealed this  
Twenty-eighth Day of May, 2013

Teresa Stanek Rea  
*Acting Director of the United States Patent and Trademark Office*